United States Patent
Keller et al.

(10) Patent No.: US 10,161,004 B2
(45) Date of Patent: Dec. 25, 2018

(54) DIAGNOSTIC MIRNA PROFILES IN MULTIPLE SCLEROSIS

(71) Applicants: Siemens Aktiengesellschaft, München (DE); Siemens Healthcare Diagnostics Holding GmbH, Eschborn (DE)

(72) Inventors: Andreas Keller, Püttlingen (DE); Eckart Meese, Hütschenhausen (DE); Cord Friedrich Stähler, Hirschberg an der Bergstraße (DE); Andreas Kappel, Glasshütten (DE); Petra Leidinger, Wadern (DE); Christina Backes, Saarbrücken (DE)

(73) Assignee: Siemens Aktiengesellschaft, Munich (DE)

( * ) Notice: Subject to any disclaimer, the term of this patent is extended or adjusted under 35 U.S.C. 154(b) by 0 days.

(21) Appl. No.: 14/396,827

(22) PCT Filed: Apr. 18, 2013

(86) PCT No.: PCT/EP2013/058036
§ 371 (c)(1),
(2) Date: Oct. 24, 2014

(87) PCT Pub. No.: WO2013/160176
PCT Pub. Date: Oct. 31, 2013

(65) Prior Publication Data
US 2015/0111772 A1  Apr. 23, 2015

(30) Foreign Application Priority Data
Apr. 27, 2012 (EP) .................. 12165918.9

(51) Int. Cl.
*C12Q 1/6883* (2018.01)
*C12Q 1/68* (2018.01)
*A61K 38/21* (2006.01)

(52) U.S. Cl.
CPC ...... *C12Q 1/6883* (2013.01); *C12Q 2600/118* (2013.01); *C12Q 2600/158* (2013.01); *C12Q 2600/178* (2013.01)

(58) Field of Classification Search
None
See application file for complete search history.

(56) References Cited

U.S. PATENT DOCUMENTS

2010/0317713 A1   12/2010   Olson et al.

FOREIGN PATENT DOCUMENTS

| WO | WO-2010/139811 A1 | 12/2010 |
|---|---|---|
| WO | WO-2011/163214 A2 | 12/2011 |
| WO | WO-2013/135581 A1 | 9/2013 |
| WO | WO-2014/001400 A1 | 1/2014 |

OTHER PUBLICATIONS

Supplementary Table 1 from Keller et al (PLoS ONE 4(10): e7440) 50 pages in Table.*
Keller et al (Mol. BioSyst., 2011, 7, 3187-3199) (Year: 2011).*
Qizilbash et al (Clinical Therapeutics 34(1): 159-176, 2012) (Year: 2012).*
Duddy et al (Neurol (2011) 258:728-739) (Year: 2011).*
Junker, A. (2011), "Pathophysiology of translational regulation by microRNAs in multiple sclerosis", *FEBS Letters*, 585: 3738-3746.
Keller, A., et al. (2009) "Multiple Sclerosis: MicroRNA Expression Profiles Accurately Differentiate Patients with Relapsing-Remitting Disease from Healthy Controls", *PLoS ONE*, 4(10): e7440, 1-7.
Martinelli-Boneschi, F., et al. (2012) "MicroRNA and mRNA expression profile screening in multiple sclerosis patients to unravel novel pathogenic steps and identify potential biomarkers" *Neuroscience Letters*, 508: 4-8.
Siegel, S., et al. (2012), "Circulating microRNAs involved in multiple sclerosis", *Molecular Biology Reports*, 39: 6219-6225.
International Search Report and Written Opinion dated Jul. 9, 2013 issued in PCT Patent Application No. PCT/EP2013/058036.
Changsheng, Du et al., (2009) "MicroRNA miR-326 regulates TH-17 differentiation and is associated with the pathogenesis of multiple sclerosis", Nature Immunology; 10:12.

* cited by examiner

Primary Examiner — Richard A Schnizer
(74) Attorney, Agent, or Firm — Harness, Dickey and Pierce, P.L.C.

(57) ABSTRACT

The invention relates to methods for diagnosing multiple sclerosis with miRNA markers. Diagnosis of multiple sclerosis (MS) can be challenging in patients with atypical presentations and during a first neurological deficit possibly related to inflammatory demyelination. Towards the identification of biomarkers for diagnosis of MS, a comprehensive analysis of miRNA expression patterns was obtained. Significantly deregulated miRNAs were identified, which have previously not been related to MS according to the microRNA disease database. These miRNAs could potentially serve as future diagnostic biomarkers for MS and help in diagnosis, monitoring disease activity, and evaluation of treatment responses in patients with MS.

6 Claims, 6 Drawing Sheets
Specification includes a Sequence Listing.

SEQUENCE LISTING

<160> NUMBER OF SEQ ID NOS: 8

<210> SEQ ID NO 1
<211> LENGTH: 22
<212> TYPE: RNA
<213> ORGANISM: Homo sapiens
<220> FEATURE:
<221> NAME/KEY: source
<222> LOCATION: 1..22
<223> OTHER INFORMATION: /mol_type="RNA"
      /note="hsa-miR-22-5p"
      /organism="Homo sapiens"

<400> SEQUENCE: 1
aguucuucag uggcaagcuu ua                                                  22

<210> SEQ ID NO 2
<211> LENGTH: 22
<212> TYPE: RNA
<213> ORGANISM: Homo sapiens
<220> FEATURE:
<221> NAME/KEY: source
<222> LOCATION: 1..22
<223> OTHER INFORMATION: /mol_type="RNA"
      /note="hsa-miR-125b-5p"
      /organism="Homo sapiens"

<400> SEQUENCE: 2
ucccugagac ccuaacuugu ga                                                  22

<210> SEQ ID NO 3
<211> LENGTH: 21
<212> TYPE: RNA
<213> ORGANISM: Homo sapiens
<220> FEATURE:
<221> NAME/KEY: source
<222> LOCATION: 1..21
<223> OTHER INFORMATION: /mol_type="RNA"
      /note="hsa-miR-629-5p"
      /organism="Homo sapiens"

<400> SEQUENCE: 3
uggguuuacg uugggagaac u                                                   21

<210> SEQ ID NO 4
<211> LENGTH: 22
<212> TYPE: RNA
<213> ORGANISM: Homo sapiens
<220> FEATURE:
<221> NAME/KEY: source
<222> LOCATION: 1..22
<223> OTHER INFORMATION: /mol_type="RNA"
      /note="hsa-miR-16-2-3p"
      /organism="Homo sapiens"

<400> SEQUENCE: 4
ccaauauuac ugugcugcuu ua                                                  22

<210> SEQ ID NO 5
<211> LENGTH: 22
<212> TYPE: RNA
<213> ORGANISM: Homo sapiens
<220> FEATURE:
<221> NAME/KEY: source
<222> LOCATION: 1..22
<223> OTHER INFORMATION: /mol_type="RNA"
      /note="hsa-miR-100-5p"
      /organism="Homo sapiens"

<400> SEQUENCE: 5

```
aacccguaga uccgaacuug ug                                        22

<210> SEQ ID NO 6
<211> LENGTH: 23
<212> TYPE: RNA
<213> ORGANISM: Homo sapiens
<220> FEATURE:
<221> NAME/KEY: source
<222> LOCATION: 1..23
<223> OTHER INFORMATION: /mol_type="RNA"
      /note="hsa-miR-20a-5p"
      /organism="Homo sapiens"

<400> SEQUENCE: 6
uaaagugcuu auagugcagg uag                                       23

<210> SEQ ID NO 7
<211> LENGTH: 21
<212> TYPE: RNA
<213> ORGANISM: Homo sapiens
<220> FEATURE:
<221> NAME/KEY: source
<222> LOCATION: 1..21
<223> OTHER INFORMATION: /mol_type="RNA"
      /note="hsa-miR-151a-3p"
      /organism="Homo sapiens"

<400> SEQUENCE: 7
cuagacugaa gcuccuugag g                                         21

<210> SEQ ID NO 8
<211> LENGTH: 22
<212> TYPE: RNA
<213> ORGANISM: Homo sapiens
<220> FEATURE:
<221> NAME/KEY: source
<222> LOCATION: 1..22
<223> OTHER INFORMATION: /mol_type="RNA"
      /note="hsa-miR-7-1-3p"
      /organism="Homo sapiens"

<400> SEQUENCE: 8
caacaaauca cagucugcca ua                                        22
```

DIAGNOSTIC MIRNA PROFILES IN MULTIPLE SCLEROSIS

PRIORITY STATEMENT

This application is a national phase patent application under 35 U.S.C. § 371 of PCT International Application No. PCT/EP2013/058036 which has an International filing date of 18 Apr. 2013, which designated the United States of America, and which claims priority to European patent application number EP 12165918.9 filed 27 Apr. 2012, the entire contents of each of which are hereby incorporated herein by reference.

REFERENCE TO A SEQUENCE LISTING

This application contains references to amino acid sequences and/or nucleic acid sequences which have been submitted concurrently herewith as the sequence listing text file "2280602.1.txt", file size 2.19 KiloBytes (KB), created on 20 Oct. 2014. The aforementioned sequence listing is hereby incorporated by reference in its entirety pursuant to 37 C.F.R. § 1.52(e)(5).

FIELD OF THE INVENTION

The invention relates to a method of diagnosis of multiple sclerosis.

BACKGROUND OF THE INVENTION

Very recently, molecular diagnostics has increasingly gained in importance. It has found an entry into the clinical diagnosis of diseases (inter alia detection of infectious pathogens, detection of mutations of the genome, detection of diseased cells and identification of risk factors for predisposition to a disease).

In particular, through the determination of gene expression in tissues, nucleic acid analysis opens up very promising new possibilities in the study and diagnosis of disease.

Nucleic acids of interest to be detected include genomic DNA, expressed mRNA and other RNAs such as MicroRNAs (abbreviated miRNAs). MiRNAs are a new class of small RNAs with various biological functions (A. Keller et al., Nat Methods. 2011 8(10):841-3). They are short (average of 20-24 nucleotide) ribonucleic acid (RNA) molecules found in eukaryotic cells. Several hundred different species of microRNAs (i.e. several hundred different sequences) have been identified in mammals. They are important for post-transcriptional gene-regulation and bind to complementary sequences on target messenger RNA transcripts (mRNAs), which can lead to translational repression or target degradation and gene silencing. As such they can also be used as biologic markers for research, diagnosis and therapy purposes.

Multiple sclerosis (MS) is an inflammatory autoimmune disease of the central nervous system, in which the myelin sheaths around the axons of the brain and spinal cord are damaged, leading to demyelination and scarring as well as a broad spectrum of clinical signs and symptoms. MS can be classified into different disease subtypes, including relapsing/remitting MS (RRMS), secondary progressive MS, primary progressive MS, progressive relapsing MS. The relapsing-remitting subtype is characterized by unpredictable relapses followed by periods of months to years of relative quiet (remission) with no new signs of disease activity. The relapsing-remitting subtype usually begins with a clinically isolated syndrome (CIS). In CIS, a patient has an attack suggestive of demyelination. Often CIS marks the onset of MS.

The diagnosis of multiple sclerosis usually involves analysis of different clinical data, imaging data, and laboratory data. Some patients live years with MS before receiving a diagnosis of disease.

Symptoms can be similar to other diseases and medical problems. Clinical, imaging, laboratory and radiologic data of the dissemination of MS lesions need to be obtained for a diagnosis, which can be time consuming, expensive and difficult. Testing of cerebrospinal fluid (CSF) can be performed to aid in diagnosing MS, however, this involves the unpleasant and risky procedure of lumbar puncture to obtain CSF.

Therefore, there exists an unmet need for an efficient, simple, reliable diagnostic test for MS.

SUMMARY OF THE INVENTION

The technical problem underlying the present invention is to provide biological markers allowing to diagnose multiple sclerosis, predict the risk of developing multiple sclerosis, or predict an outcome of multiple sclerosis.

Before the invention is described in detail, it is to be understood that this invention is not limited to the particular component parts of the process steps of the methods described as such methods may vary. It is also to be understood that the terminology used herein is for purposes of describing particular embodiments only, and is not intended to be limiting. It must be noted that, as used in the specification and the appended claims, the singular forms "a," "an" and "the" include singular and/or plural referents unless the context clearly dictates otherwise. It is also to be understood that plural forms include singular and/or plural referents unless the context clearly dictates otherwise. It is moreover to be understood that, in case parameter ranges are given which are delimited by numeric values, the ranges are deemed to include these limitation values.

In its most general terms, the invention relates to a collection of miRNA markers useful for the diagnosis, prognosis and prediction of multiple sclerosis, in particular of CIS/RRMS.

The invention relates to a method for diagnosing multiple sclerosis, predicting risk of developing multiple sclerosis, or predicting an outcome of multiple sclerosis, said method comprising the steps of:

a) determining in a sample from said patient, the expression level of at least one miRNA selected from the group consisting of hsa-miR-16-2-3p, hsa-miR-22-5p, hsa-miR-125b-5p, hsa-miR-629-5p, hsa-miR-100-5p, hsa-miR-20a-5p, hsa-miR-151a-3p, and hsa-miR-7-1-3p.

b) comparing the pattern of expression level(s) determined in step a) with one or several reference pattern(s) of expression levels; and c) diagnosing multiple sclerosis, predicting a risk of developing multiple sclerosis, or predicting an outcome of multiple sclerosis from the outcome of the comparison in step b).

Further the invention relates to a method of classifying a sample of a patient suffering from or at risk of developing a multiple sclerosis, said method comprising the steps of:

a) determining in said sample from said patient, the expression level of at least one miRNA selected from the group consisting of hsa-miR-16-2-3p, hsa-miR-22-5p, hsa-miR-125b-5p, hsa-miR-629-5p, hsa-miR-100-5p, hsa-miR-20a-5p, hsa-miR-151a-3p, and hsa-miR-7-1-3p.

b) comparing the pattern of expression level(s) determined in step a) with one or several reference pattern(s) of expression levels; and c) classifying the sample of said patient from the outcome of the comparison in step b) into one of at least two classes.

Such classification can be indicative of a diagnosis of multiple sclerosis, of predicting a risk of developing multiple sclerosis, or of predicting an outcome of multiple sclerosis Said classes may be healthy/diseased, low risk/high risk, low risk/high risk of developing disease or the like.

Preferably, the expression level of 2, 3, 4, 5, 6, 7, or 8 miRNAs selected from the group consisting of hsa-miR-16-2-3p, hsa-miR-22-5p, hsa-miR-125b-5p, hsa-miR-629-5p, hsa-miR-100-5p, hsa-miR-20a-5p, hsa-miR-151a-3p, and hsa-miR-7-1-3p can be determined in said sample from said patient.

A reference pattern of expression levels may be obtained by determining in at least one healthy subject the expression level of at least one miRNA selected from the group consisting of hsa-miR-16-2-3p, hsa-miR-22-5p, hsa-miR-125b-5p, hsa-miR-629-5p, hsa-miR-100-5p, hsa-miR-20a-5p, hsa-miR-151a-3p, and hsa-miR-7-1-3p.

It is within the scope of the invention to assign a numerical value to an expression level of the at least one miRNA determined in step a).

It is further within the scope of the invention to apply an algorithm to perform step b) by applying an algorithm to obtain a normalized expression level relative to a reference pattern of expression level(s).

It is within the scope of the invention to apply an algorithm to the numerical value of the expression level of the at least one miRNA determined in step a) to obtain a disease score to allow classification of the sample or diagnosis, prognosis or prediction of the risk of developing multiple sclerosis, or prediction of an outcome of multiple sclerosis. A non-limiting example of such an algorithm is to compare the numerical value of the expression level against a threshold value in order to classify the result into one of two categories, such as high risk/low risk, diseased/healthy or the like. A further non-limiting example of such an algorithm is to combine a plurality of numerical values of expression levels, e.g. by summation, to obtain a combined score. Individual summands may be normalized or weighted by multiplication with factors or numerical values representing the expression level of an miRNA, numerical values representing clinical data, or other factors.

It is within the scope of the invention to apply a discriminant function to classify a result, diagnose disease, or predict an outcome or a risk.

According to an aspect of the invention, the sample is selected from the group consisting of blood sample, serum sample, and plasma sample.

According to a further Aspect of the invention the sample is a blood sample.

According to an aspect of the invention the methods of the invention comprise in step a) determining the expression level of the miRNAs: hsa-miR-16-2-3p, hsa-miR-20a-5p, and hsa-miR-7-1-3p.

According to an aspect of the invention the methods of the invention comprise in step a) determining the expression level of the miRNAs: hsa-miR-22-5p, hsa-miR-125b-5p, hsa-miR-16-2-3p, hsa-miR-100-5p, hsa-miR-20a-5p, hsa-miR-151a-3p, and hsa-miR-7-1-3p.

According to an aspect of the invention the methods of the invention comprise in step a) determining the expression level of all miRNAs selected from the group consisting of hsa-miR-22-5p, hsa-miR-125b-5p, hsa-miR-629-5p, hsa-miR-16-2-3p, hsa-miR-100-5p, hsa-miR-20a-5p, hsa-miR-151a-3p, and hsa-miR-7-1-3p.

The invention further relates to a kit for diagnosing multiple sclerosis, predicting risk of developing multiple sclerosis, or predicting an outcome of multiple sclerosis in a patient suffering from or at risk of developing multiple sclerosis, said kit comprising means for determining in said sample from said patient, an expression level of at least one miRNA selected from the group consisting of hsa-miR-22-5p, hsa-miR-125b-5p, hsa-miR-629-5p, hsa-miR-16-2-3p, hsa-miR-100-5p, hsa-miR-20a-5p, hsa-miR-151a-3p, and hsa-miR-7-1-3p, at least one reference pattern of expression levels for comparing with the expression level of the at least one miRNA from said sample.

The means for determining the expression level of said at least one miRNA may comprise an oligonucleotide probe for detecting or amplifying said at least one miRNA, means for determining the expression level based on an array-based method, a PCR based method, a sequencing based method or any other suitable means for determining the expression level.

The reference expression level pattern may be supplied as numeric information, in particular as computer encoded information on any suitable information carrier.

The invention further relates to a computer program product for diagnosing multiple sclerosis, predicting risk of developing multiple sclerosis, or predicting an outcome of multiple sclerosis in a patient suffering from or at risk of developing multiple sclerosis, comprising means for receiving data representing an expression level of at least one miRNA in a patient sample selected from the group consisting of hsa-miR-16-2-3p, hsa-miR-22-5p, hsa-miR-125b-5p, hsa-miR-629-5p, hsa-miR-100-5p, hsa-miR-20a-5p, hsa-miR-151a-3p, and hsa-miR-7-1-3p, means for receiving data representing at least one reference pattern of expression levels for comparing with the expression level of the at least one miRNA from said sample, means for comparing said data representing the expression level of the at least one miRNA in a patient sample means for determining a diagnosis of multiple sclerosis, a prediction of a risk of developing multiple sclerosis, or a prediction of an outcome of multiple sclerosis from the outcome of the comparison in step b).

The computer program product may be provided on a storable electronic medium, such as a solid state memory, disk, CD or other. It may be stored locally on a computer. It may be implemented as network-based program or application, including a web- or internet-based application. It may be implemented in a diagnostic device, such as an analyzer instrument. It may be operably connected to a device for outputting information, such as a display, printer or the like.

Further herein disclosed is a method for identifying an miRNA biomarker for diagnosing a disease, predicting a risk of developing said disease, or predicting an outcome of said disease in a patient, comprising the following steps:

a) identifying a plurality of miRNAs which are differentially expressed at least one sample of a patient suffering from said disease compared to at least one reference sample by using a high throughput sequencing method, b) identifying a further plurality of miRNAs which are differentially expressed in a further sample of a further patient suffering from said disease compared to a further reference sample by using a nucleic acid array, c) comparing the plurality of miRNAs identified in step (a) and the further plurality of miRNAs identified in step (b) to identify at least one miRNA which is differentially expressed in both (a) and (b), and, optionally, d) confirming differential expression of said at least one miRNA by a PCR based method.

DETAILED DESCRIPTION OF THE INVENTION

Definitions

Figure 1:
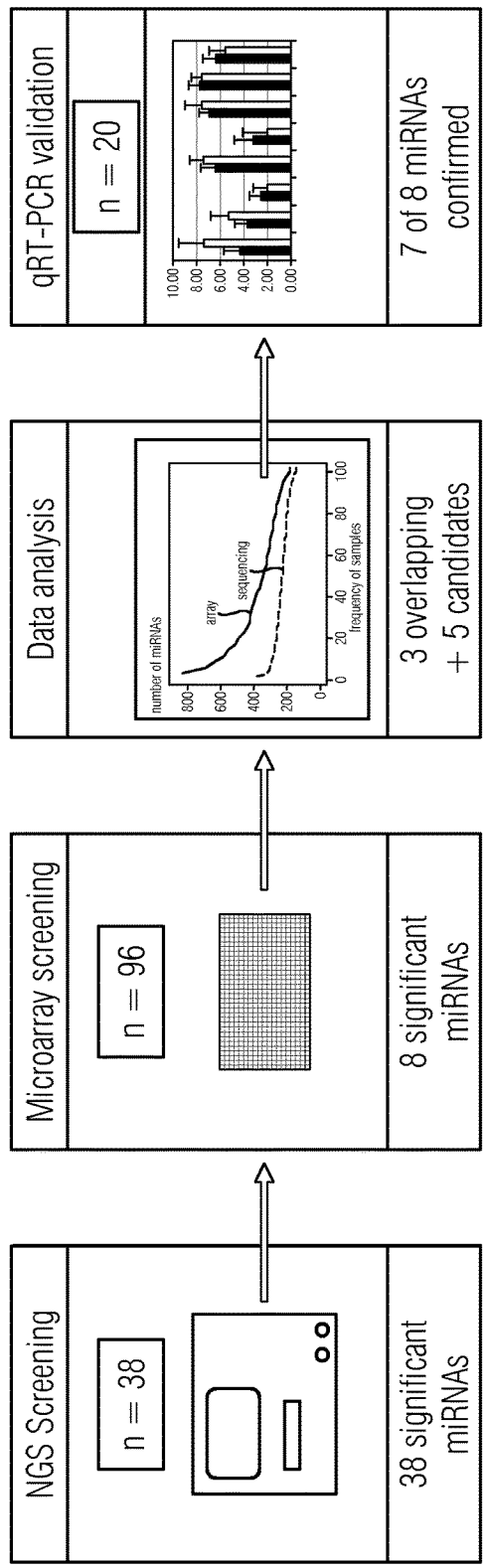
FIG. 1: Project overview. Three experimental methods including NGS, microarray, and qRT-PCR were applied to comprehensively analyze miRNA expression in patients with CIS/RRMS.

Unless defined otherwise, technical and scientific terms used herein have the same meaning as commonly understood by one of ordinary skill in the art to which this invention belongs.

The term "multiple sclerosis" or "MS" as used herein relates to an inflammatory disease of the nervous system and is meant to include all clinical stages and subtypes of disease, including clinically isolated symptoms of MS (CIS), relapsing/remitting MS (RRMS), secondary progressive MS, primary progressive MS, and progressive relapsing MS.

The term "predicting an outcome" of a disease, as used herein, is meant to include both a prediction of an outcome of a patient undergoing a given therapy and a prognosis of a patient who is not treated.

An "outcome" within the meaning of the present invention is a defined condition attained in the course of the disease. This disease outcome may e.g. be a clinical condition such as "relapse of disease", "remission of disease", "response to therapy", a disease stage or grade or the like.

A "risk" is understood to be a probability of a subject or a patient to develop or arrive at a certain disease outcome. The term "risk" in the context of the present invention is not meant to carry any positive or negative connotation with regard to a patient's wellbeing but merely refers to a probability or likelihood of an occurrence or development of a given event or condition.

The term "clinical data" relates to the entirety of available data and information concerning the health status of a patient including, but not limited to, age, sex, weight, menopausal/hormonal status, etiopathology data, anamnesis data, data obtained by in vitro diagnostic methods such as blood or urine tests, data obtained by imaging methods, such as x-ray, computed tomography, MRI, PET, spect, ultrasound, electrophysiological data, genetic analysis, gene expression analysis, biopsy evaluation, intraoperative findings.

The term "classification of a sample" of a patient, as used herein, relates to the association of said sample with at least one of at least two categories. These categories may be for example "high risk" and "low risk", high, intermediate and low risk, wherein risk is the probability of a certain event occurring in a certain time period, e.g. occurrence of disease, progression of disease, etc. It can further mean a category of favorable or unfavorable clinical outcome of disease, responsiveness or non-responsiveness to a given treatment or the like. Classification may be performed by use of an algorithm, in particular a discriminant function. A simple example of an algorithm is classification according to a first quantitative parameter, e.g. expression level of a nucleic acid of interest, being above or below a certain threshold value. Classification of a sample of a patient may be used to predict an outcome of disease or the risk of developing a disease. Instead of using the expression level of a single nucleic acid of interest, a combined score of several nucleic acids of interest of interest may be used. Further, additional data may be used in combination with the first quantitative parameter. Such additional data may be clinical data from the patient, such as sex, age, weight of the patient, disease grading etc.

A "discriminant function" is a function of a set of variables used to classify an object or event. A discriminant function thus allows classification of a patient, sample or event into a category or a plurality of categories according to data or parameters available from said patient, sample or event. Such classification is a standard instrument of statistical analysis well known to the skilled person. E.g. a patient may be classified as "high risk" or "low risk", "in need of treatment" or "not in need of treatment" or other categories according to data obtained from said patient, sample or event. Classification is not limited to "high vs. low", but may be performed into a plurality of categories, grading or the like. Examples for discriminant functions which allow a classification include, but are not limited to discriminant functions defined by support vector machines (SVM), k-nearest neighbors (kNN), (naive) Bayes models, or piece-wise defined functions such as, for example, in subgroup discovery, in decision trees, in logical analysis of data (LAD) an the like.

The term "expression level" refers, e.g., to a determined level of expression of a nucleic acid of interest. The term "pattern of expression levels" refers to a determined level of expression compared either to a reference nucleic acid, e.g. from a control, or to a computed average expression value, e.g. in DNA-chip analyses. A pattern is not limited to the comparison of two genes but is also related to multiple comparisons of genes to reference genes or samples. A certain "pattern of expression levels" may also result and be determined by comparison and measurement of several nucleic acids of interest disclosed hereafter and display the relative abundance of these transcripts to each other. Expression levels may also be assessed relative to expression in different tissues, patients versus healthy controls, etc.

A "reference pattern of expression levels", within the meaning of the invention shall be understood as being any pattern of expression levels that can be used for the comparison to another pattern of expression levels. In a preferred embodiment of the invention, a reference pattern of expression levels is, e.g., an average pattern of expression levels observed in a group of healthy or diseased individuals, serving as a reference group.

In the context of the present invention a "sample" or a "biological sample" is a sample which is derived from or has been in contact with a biological organism. Examples for biological samples are: cells, tissue, body fluids, biopsy specimens, blood, urine, saliva, sputum, plasma, serum, cell culture supernatant, and others.

A "probe" is a molecule or substance capable of specifically binding or interacting with a specific biological molecule. The term "primer", "primer pair" or "probe", shall have ordinary meaning of these terms which is known to the person skilled in the art of molecular biology. In a preferred embodiment of the invention "primer", "primer pair" and "probes" refer to oligonucleotide or polynucleotide molecules with a sequence identical to, complementary too, homologues of, or homologous to regions of the target molecule or target sequence which is to be detected or quantified, such that the primer, primer pair or probe can specifically bind to the target molecule, e.g. target nucleic acid, RNA, DNA, cDNA, gene, transcript, peptide, polypeptide, or protein to be detected or quantified. As understood herein, a primer may in itself function as a probe. A "probe" as understood herein may also comprise e.g. a combination of primer pair and internal labeled probe, as is common in many commercially available qPCR methods.

A "gene" is a set of segments of nucleic acid that contains the information necessary to produce a functional RNA product in a controlled manner. A "gene product" is a biological molecule produced through transcription or expression of a gene, e.g. an mRNA or the translated protein.

An "miRNA" is a short, naturally occurring RNA molecule and shall have the ordinary meaning understood by a person skilled in the art. A "molecule derived from an miRNA" is a molecule which is chemically or enzymatically obtained from an miRNA template, such as cDNA.

The term "array" refers to an arrangement of addressable locations on a device, e.g. a chip device. The number of locations can range from several to at least hundreds or thousands. Each location represents an independent reaction site. Arrays include, but are not limited to nucleic acid arrays, protein arrays and antibody-arrays. A "nucleic acid array" refers to an array containing nucleic acid probes, such as oligonucleotides, polynucleotides or larger portions of genes. The nucleic acid on the array is preferably single stranded. A "microarray" refers to a biochip or biological chip, i.e. an array of regions having a density of discrete regions with immobilized probes of at least about 100/cm2.

A "PCR-based method" refers to methods comprising a polymerase chain reaction PCR. This is a method of exponentially amplifying nucleic acids, e.g. DNA or RNA by enzymatic replication in vitro using one, two or more primers. For RNA amplification, a reverse transcription may be used as a first step. PCR-based methods comprise kinetic or quantitative PCR (qPCR) which is particularly suited for the analysis of expression levels,). When it comes to the determination of expression levels, a PCR based method may for example be used to detect the presence of a given mRNA by (1) reverse transcription of the complete mRNA pool (the so called transcriptome) into cDNA with help of a reverse transcriptase enzyme, and (2) detecting the presence of a given cDNA with help of respective primers. This approach is commonly known as reverse transcriptase PCR (rtPCR). The term "PCR based method" comprises both end-point PCR applications as well as kinetic/real time PCR techniques applying special fluorophors or intercalating dyes which emit fluorescent signals as a function of amplified target and allow monitoring and quantification of the target. Quantification methods could be either absolute by external standard curves or relative to a comparative internal standard.

The term "next generation sequencing" or "high throughput sequencing" refers to high-throughput sequencing technologies that parallelize the sequencing process, producing thousands or millions of sequences at once. Examples include Massively Parallel Signature Sequencing (MPSS) Polony sequencing, 454 pyrosequencing, Illumina (Solexa) sequencing, SOLiD sequencing, Ion semiconductor sequencing, DNA nanoball sequencing, Helioscope™ single molecule sequencing, Single Molecule SMRT™ sequencing, Single Molecule real time (RNAP) sequencing, Nanopore DNA sequencing.

The term "marker" or "biomarker" refers to a biological molecule, e.g., a nucleic acid, peptide, protein, hormone, etc., whose presence or concentration can be detected and correlated with a known condition, such as a disease state, or with a clinical outcome, such as response to a treatment.

Additional details, features, characteristics and advantages of the object of the invention are further disclosed in the following description and figures of the respective examples, which, in an exemplary fashion, show preferred embodiments of the present invention. However, these examples should by no means be understood as to limit the scope of the invention.

The invention relates to methods for diagnosing multiple sclerosis with miRNA markers.

Diagnosis of multiple sclerosis (MS) can be challenging in patients with atypical presentations and during a first neurological deficit possibly related to inflammatory demyelination. In particular, it is difficult to diagnose CIS/RRMS, which often presents the earliest stage of disease. However, it would be particularly desirable to have a reliable diagnostic test for this stage of disease, as the chance of therapeutic intervention is better during this early disease stage. RRMS is challenging to diagnose because of the many different neurologic symptoms with which it can present. Towards the identification of biomarkers for diagnosis of MS, a comprehensive analysis of miRNA expression patterns in whole blood samples from treatment-naive patients with a clinically isolated syndrome (CIS) or relapsing-remitting MS (RRMS) and matched controls by using Next Generation Sequencing, microarray analysis, and qRT-PCR was obtained. In patients with CIS/RRMS significantly deregulated miRNAs were identified, which have previously not been related to MS according to the microRNA disease database. These miRNAs could potentially serve as future diagnostic biomarkers for MS and help in diagnosis, monitoring disease activity, and evaluation of treatment responses in patients with MS.

Figure 2:
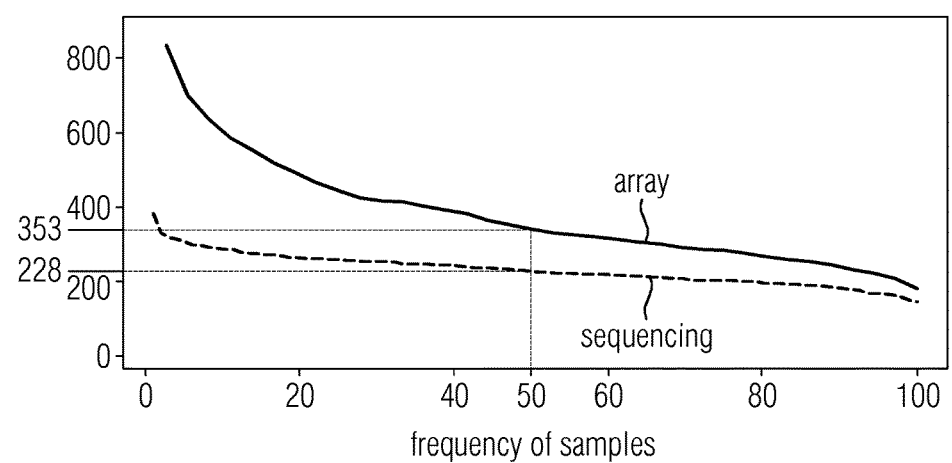
FIG. 2: Number of miRNAs and the frequency of samples in which these miRNAs were detected. The blue curve indicates the results of the NGS, the red curve indicates the results of the microarrays. By NGS 353 miRNAs were detectable in at least half of all investigated samples, by microarray analysis 228 miRNAs were detectable in at least half of all investigated samples (see dashed lines).
Figure 3:
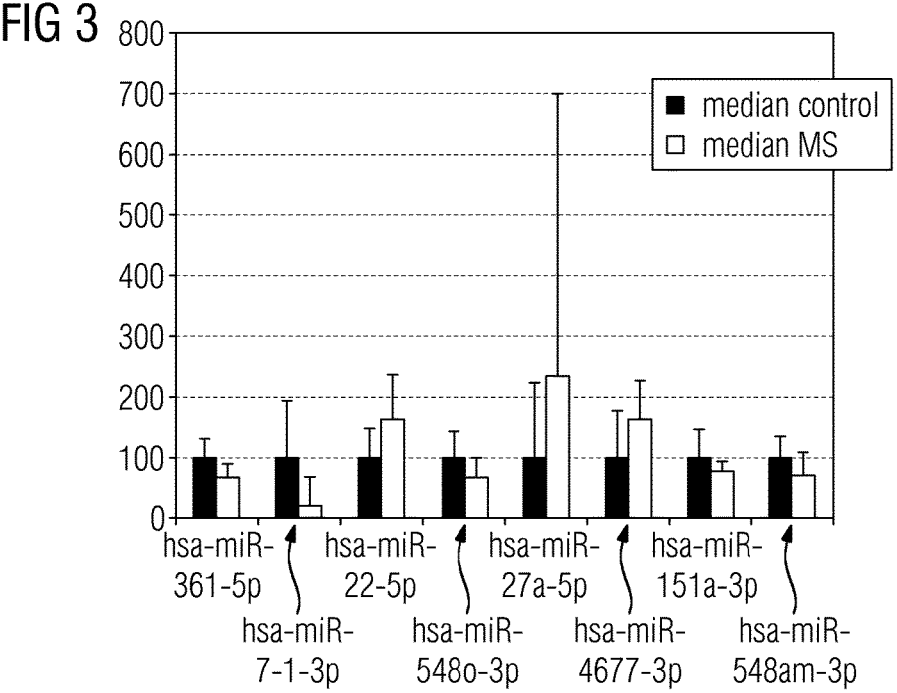
FIG. 3: The 8 most deregulated miRNAs (p-value<0.01) identified by NGS. On the x-axis, the bars for the median of the control samples (black) and for the median of the MS samples (light grey) of the 8 different miRNAs with their standard deviation are indicated, the y-axis presents the read counts.
Figure 4:
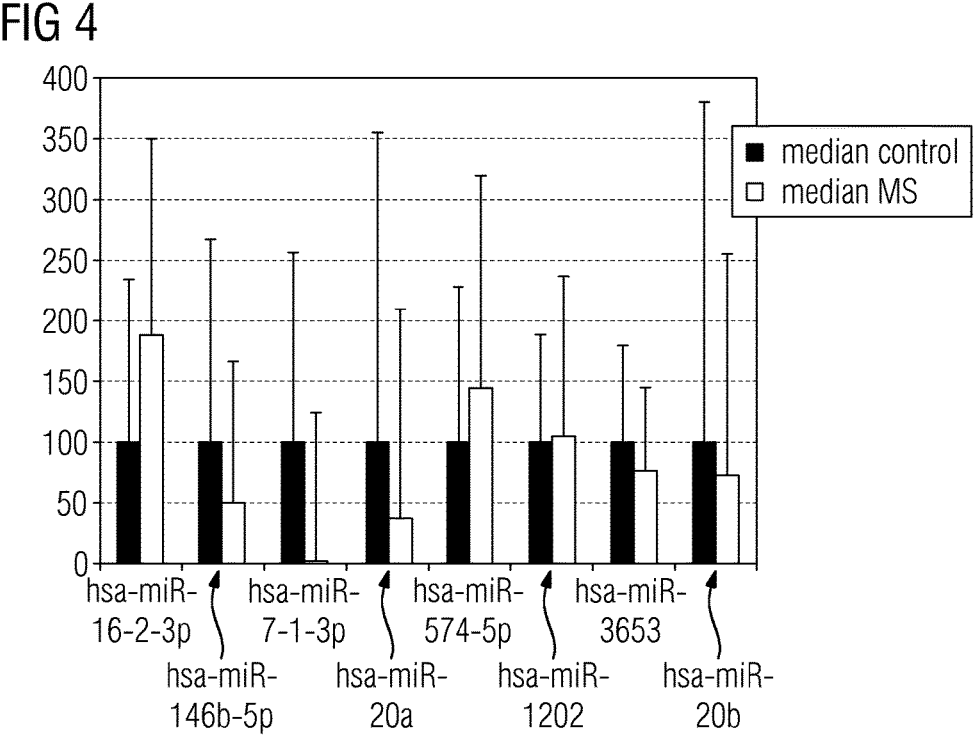
FIG. 4: The 8 most deregulated miRNAs (p-value<0.01) identified by microarray analysis. On the x-axis, the bars for the median of the control samples (black) and for the median of the MS samples (light grey) of the 8 different miRNAs with their standard deviation are indicated, the y-axis presents the signal intensities.
Figure 5:
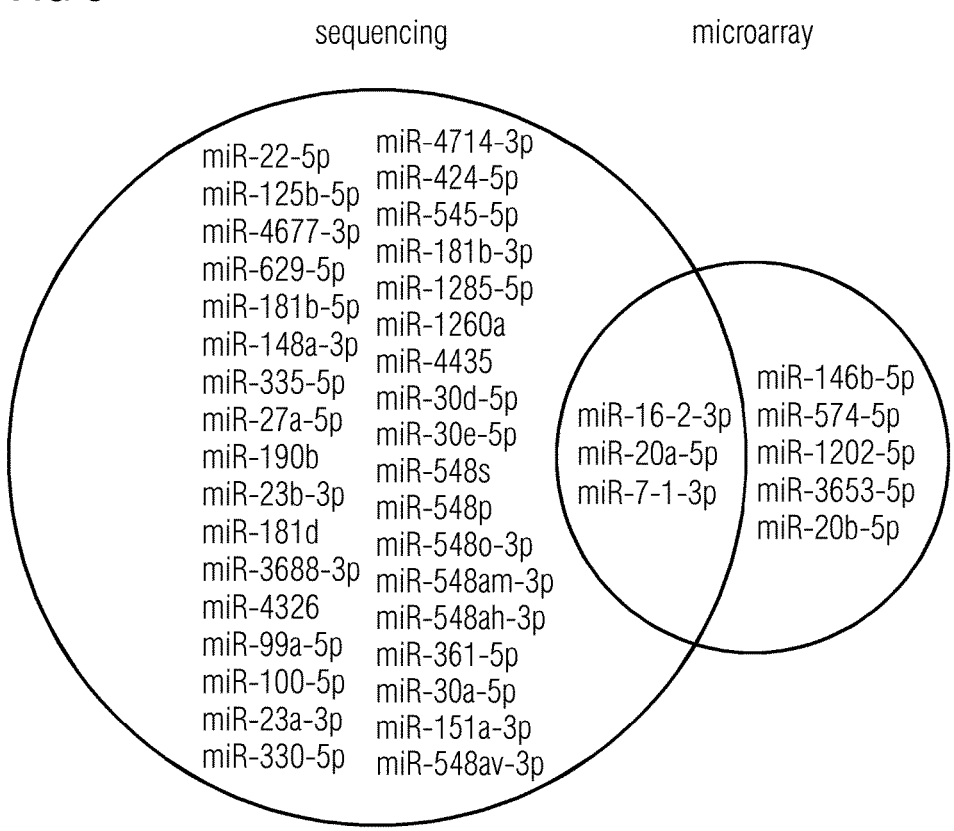
FIG. 5: Venn diagram showing the significantly deregulated miRNAs identified by NGS and microarrays. By microarray analysis we identified 8 miRNAs and by NGS we identified 38 miRNAs significantly deregulated in MS. Three miRNAs, namely hsa-miR-16-2-3p, hsa-miR-20a-3p, and hsa-miR-7-1-3p, were identified with both approaches.
Figure 6:
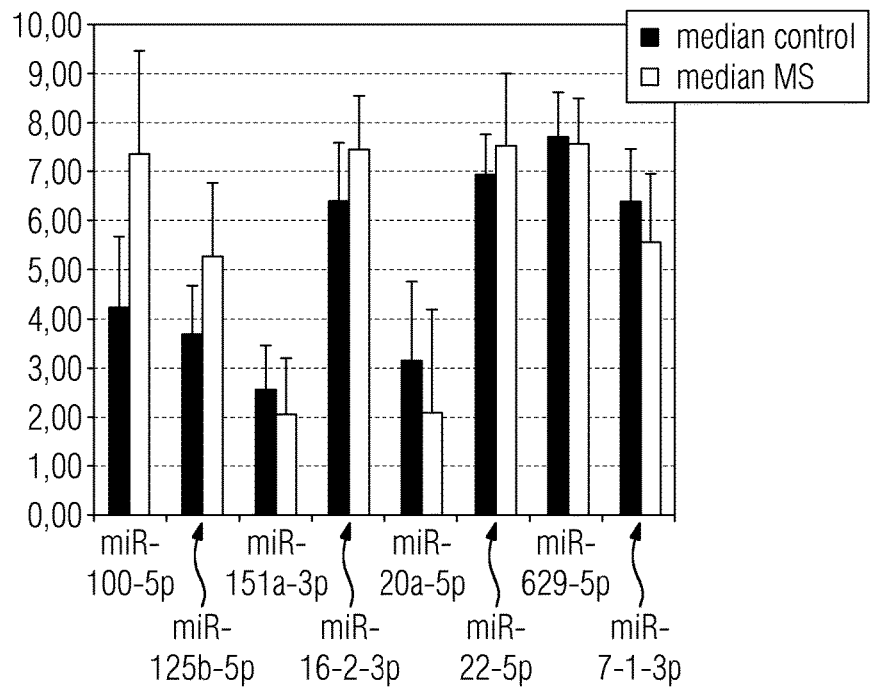
FIG. 6: qRT-PCR validation of the 8 miRNAs. The bar diagram shows the delta CT values and standard deviations for the 8 tested candidate MS markers.
Figure 7:
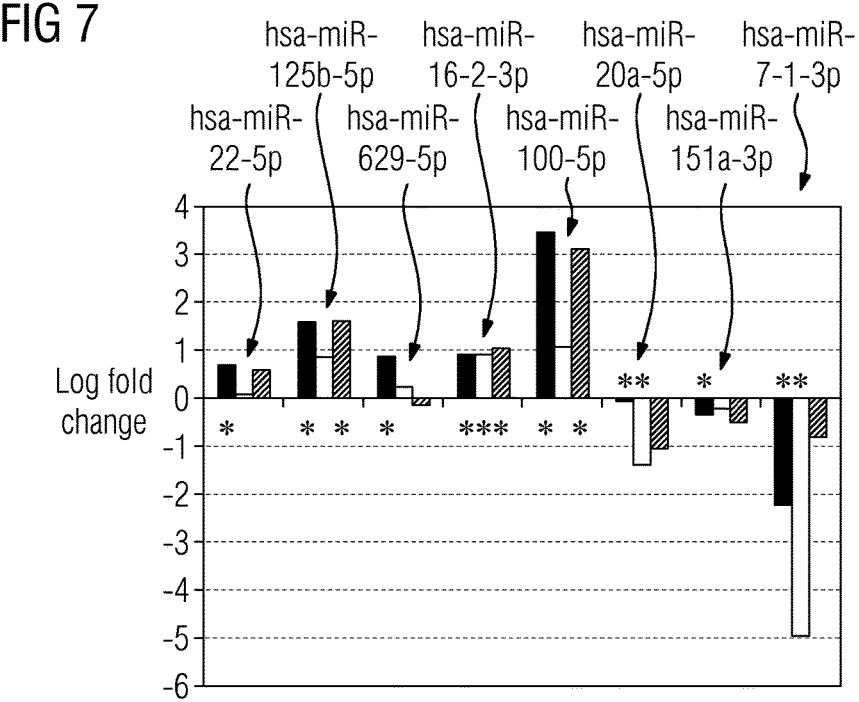
FIG. 7: Comparison of the expression analysis of the 8 miRNAs using NGS, microarray and qRT-PCR. The height of the bars represents the logarithmized fold changes of each miRNA and each used analysis method (NGS=black bars, microarray=white bars, qRT-PCR=shaded bars). We obtained the concordant results for all but one miRNA (has-miR-629-5p).

In the attached Figures,

FIG. 1 shows an overview of the methods used to indentify miRNA markers;

FIG. 2 shows the number of miRNAs and the frequency of samples in which these miRNAs were detected;

FIG. 3 shows the 8 most deregulated miRNAs identified by NGS;

FIG. 4 shows the 8 most deregulated miRNAs identified by microarray analysis;

FIG. 5 shows a Venn diagram showing the significantly deregulated miRNAs identified by NGS and microarrays;

FIG. 6 shows the qRT-PCR validation of the 8 miRNAs;

FIG. 7 shows the comparison of the expression analysis of the 8 miRNAs using NGS, microarray and qRT-PCR; and.

Figure 8:
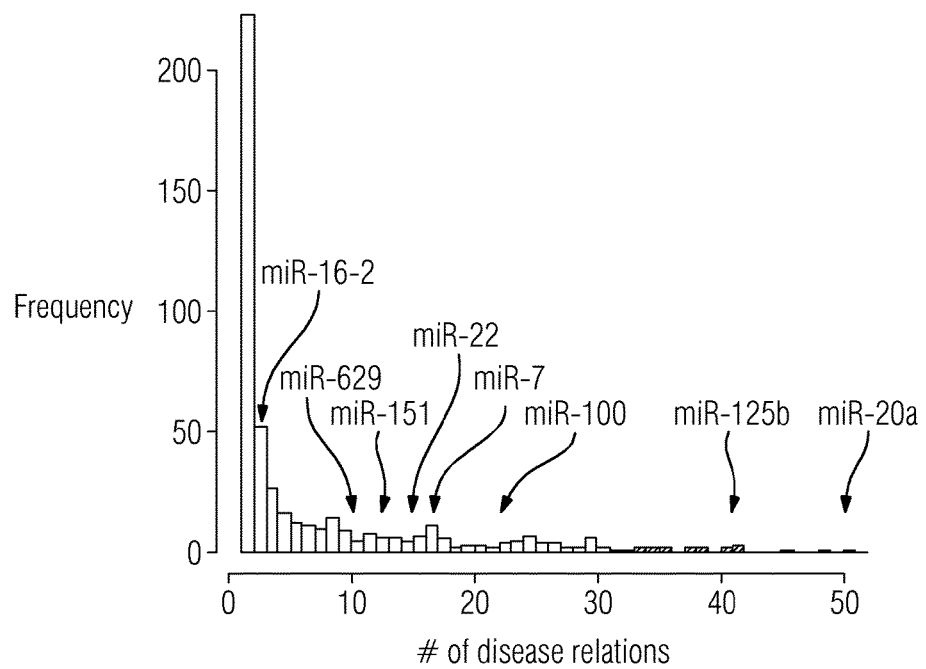
FIG. 8: Frequency of disease associations. The figure shows for all miRNAs deposited in the HMDD database the frequency of relations to diseases.

FIG. 8 shows the frequency of disease associations of examined miRNA markers.

To comprehensively analyze miRNA profiles in patients with CIS/RRMS three experimental stages, as detailed in FIG. 1, were applied. First, a screening using NGS was carried out in a cohort of 38 patients and controls, then a microarray screening using an extended cohort of 96 age and sex matched cases and controls was carried out. Analyzing both high-throughput data sets resulted in 8 miRNA candidates that were analysed in 20 individuals (5 CIS, 5 RRMS, and 10 age and sex matched controls) by qRT-PCR. Detailed characteristics of patients with CIS/RRMS and the healthy controls are presented in Table 1. To exclude immunomodulatory or immunosuppressive therapy as a confounding factor, only treatment-naive patients were included in this work.

Patients and Sample Preparation

About 5 ml of blood was collected in PAXgene Blood RNA tubes (Becton Dickinson, Heidelberg, Germany) from 50 patients with a diagnosis of a CIS (n=25) or RRMS (n=25) according to the McDonald 2005 criteria. Fifty age (+/−4 years) and gender matched healthy adults were included as controls (Table 1).

Total RNA including miRNA was isolated using the PAXgene Blood miRNA Kit (Qiagen) following the manufacturers recommendations. Isolated RNA was stored at −80° C. RNA integrity was analysed using Bioanalyzer 2100 (Agilent) and concentration and purity was measured using NanoDrop 2000 (thermo Scientific). A total of four samples (three controls and one RRMS) failed the quality criteria and were excluded from the study.

NGS Screening

Initially a high-throughput screening of 38 samples from 16 patients with CIS/RRMS and 22 controls was performed. Altogether, a total of 835 miRNAs being expressed in at least a single sample were found. FIG. 2 presents the number of miRNAs and the frequency of samples in which these miRNAs were detected (blue curve). As shown there, 353 miRNAs were detectable in at least half of all investigated samples, providing evidence for a high abundance of the respective miRNAs in the investigated blood samples. Following normalisation t-tests showed a total of 38 significantly (non-adjusted) deregulated miRNAs. The 8 most deregulated miRNAs are presented in FIG. 3 (p-value<0.01). However, after adjustment for multiple testing no miRNAs remained significant, due to the large number of features (minimal p-value was 0.155). These 8 miRNAs included 5 down-regulated miRNAs, namely hsa-miR-361-5p, hsa-miR-7-1-3p, hsa-miR-548o-3p, hsa-miR-151a-3p, and hsa-miR-548am-3p and 3 up-regulated miRNAs, namely hsa-miR-22-5p, hsa-miR-27a-5p, hsa-miR-4677-3p. Altogether, 16 of the 38 deregulated miRNAs were down-regulated while 22 were up-regulated in CIS/RRMS.

The TruSeq Small RNA sample preparation Kit (Illumina) was used to generate multiplexed sequencing libraries, which were afterwards sequenced on a HiSeq2000 System (Illumina) using the 50 bp fragment sequencing protocol. Resulting sequencing reads were demultiplexed using the CASAVA 1.8 software package (Illumina) and quality checked using FastQC tools (Babraham Inst.). A primary mapping analysis using the miRDeep2-pipeline was conducted to ensure that a significant proportion of miRNAs have been sequenced.

In total, 38 samples from n=16 patients (5 RRMS, 11 CIS) and n=22 controls were analyzed in two multiplexed pools. On average, 1.5-2 million high quality sequencing reads per sample were obtained (at a total of 95 million reads) of which up to 70% contained miRNA information.

The raw illumina reads were first preprocessed by cutting the 3' adapter sequence. This was done by the program fastx_clipper from the FASTX-Toolkit. Reads shorter than 18 nucleotides after clipping were removed. The remaining reads were collapsed, i.e. after this step only unique reads and their frequency per sample was obtained. This step reduces the time for mapping the reads enormously. For the remaining steps, the miRDeep2 pipeline was used. These steps consist of mapping the reads against the genome (hg19), mapping the reads against miRNA precursor sequences from mirbase release v18, summarizing the counts for the samples, and prediction of novel miRNAs.

Microarray Screening

Next, an extended cohort of 96 age and sex matched samples from 49 patients with CIS/RRMS and 47 controls was screened using microarrays containing 1205 miRNAs, representing the content of miRBase v16. As for the sequencing results, the number of detected miRNAs was first evaluated. As shown in the red curve in FIG. 2, significantly less (p=6.5*10−7) miRNAs were detected in the microarray study than by NGS. In at least a single sample, 382 miRNAs were detected (around 46% of the 835 miRNAs detected at least in a single sample by NGS) and 228 miRNAs were detected in at least 50% of all samples (compared to 353 miRNAs in the sequencing approach). Without wishing to be bound by this theory, it is believed that this may be due to two different reasons, first, the microarray experiments are restricted to the content of miRBase v16, while sequencing may discover all existing human miRNAs, and, in addition, the sequencing approach in general is more sensitive as compared to microarray experiments. This is also reflected by a closer analysis of the 38 significantly (non-adjusted) deregulated miRNAs identified by sequencing. Of these, 7 (18.4%) were not included on the SurePrint 8×60K Human v16 miRNA microarray, and further 14 (36.8%) miRNAs were included on the microarray but were not detected. In the microarray experiments a total of 8 significantly deregulated miRNAs were detected. As for the NGS experiments the p-values were not adjusted for multiple testing to make the values comparable between the different approaches. The respective markers are shown in FIG. 4. As for the sequencing approach, 5 miRNAs were down-regulated (hsa-miR-146b-5p, hsa-miR-7-1-3p, hsamiR-20a, hsa-miR-3653, hsa-miR-20b) and 3 were up-regulated (hsa-miR-16-2-3p, hsa-miR-574-5p, hsa-miR-1202) in patients with CIS/RRMS.

Microarray analysis was performed according to the manufacturer's instructions using SurePrint 8×60K Human v16 miRNA microarrays (Agilent, CatNo G4870A) that contain 40 replicates of each of the 1205 miRNAs of miRBase v16 (www.mirbase.org/). In brief, a total of 100 ng total RNA was processed using the miRNA Complete Labeling and Hyb Kit to generate fluorescently labeled miRNA. After the labelling reaction, the mixture is dryed in a vacuum centrifuge and resuspended in the hybridization mixture containing hybridization buffer and blocking reagent. Then the microarrays were loaded and incubated. To check if the labelling and hybridization was successful, labeling and hybridization spike-in controls were added in the appropriate steps. After several washing steps microarrays were scanned with the Agilent Microarray Scanner at 3 microns in double path mode. Microarray scan data were further processed using Feature Extraction software.

Overlap in Significantly Deregulated miRNAs Between NGS and Microarray Analyses

As described above, 38 significantly (non-adjusted) deregulated miRNAs were detected by NGS and 8 significantly (non-adjusted) deregulated miRNAs were detected by microarray analyses. These correspond to 1.9% and 0.7% of the respectively measured miRNAs, thus, a random overlap between both sets is highly unlikely. However, remarkably, there was an overlap of three miRNAs, including hsa-miR-16-2-3p, hsa-miR-20a-5p, and hsa-miR-7-1-3p (see FIG. 5). 1 million permutation tests confirmed that this overlap is highly significant (p=0.004). In addition, 5 of the 38 miRNAs identified by NGS showed the same tendency of regulation in the microarray analyses. However, the regulation of those five miRNAs, that include hsa-miR-22-5p, hsa-miR-125b-5p, hsa-miR-629-5p, hsa-miR-100-5p, and hsa-miR-151a-3p, was not statistically significant (p>0.05). The 3 significantly deregulated miRNAs identified by both methods and the 5 further miRNAs are listed in Table 2 together with their expression values in both experiments and significance values.

Analysis by qRT-PCR

The 8 miRNAs were further analyzed using qRT-PCR. Seven of the 8 miRNAs could be confirmed, however, 4 miRNAs (hsa-miR-22-5p, hsa-miR-629-5p, hsa-miR-20a-5p, and hsa-miR-151a-3p) were not significantly deregulated according to the qRT-PCR results. Hsa-miR-629-5p showed in contrast to NGS and microarray analysis a slightly but not significantly (p=0.71) higher expression in controls compared to MS patients. Table 2 also includes the results of the qRT-PCR validation. FIG. 6 shows the delta CT values and standard deviations for the qRT-PCR validation. FIG. 7 visualizes the comparison of the expression analysis of the 8 miRNAs using NGS, microarray and qRT-PCR.

A set of 20 age and gender matched patient and control samples was composed that were also used for microarray and NGS analyses. The group of patients included 5 CIS and 5 RRMS patients. For qRT-PCR validation three miRNAs significantly deregulated in both microarray and NGS were selected, and 5 miRNAs that were shown to be deregulated by NGS and that showed the same tendency of regulation, but were not significantly deregulated in the microarray analyses. The qRT-PCR was performed using Taqman qRT-PCR system (Applied Biosystems). The small RNAs RNU6B and RNU48 were used as endogenous controls.

Relevance of the 8 miRNAs

For the 8 concordant miRNAs the known disease interactions were extracted (i.e. a publication describes the respective miRNA to be dys-regulated in the considered disease) from the HMDD database (FIG. 8). Computing the number of disease interactions for each of the 8 miRNAs and comparing them to the average of 8 miRNA disease interactions a significantly increased number was found for the miRNAs described herein, i.e., the detected miRNAs are generally correlated to different diseases. All but one miRNA were correlated with more than 8 diseases, suggesting that the different miRNAs are not specific for CIS/RRMS (see FIG. 8). However, no disease with the same pattern as the CIS/RRMS miRNA set was found, indicating that this miRNA set has an increased specificity for CIS/RRMS.

By applying miRNA enrichment analysis for the precursor molecules it was found that 4 of the 8 miRNAs are associated with immune response, namely hsa-miR-20a, hsa-miR-100, hsa-miR-125b, and hsa-miR-16-2. Likewise, four miRNAs were correlated with hormone regulation, namely hsa-miR-20a, hsa-miR-7-1, hsa-miR-22, and hsa-miR-16-2. Considering disease relations, hsa-miR-100, hsa-miR-125b, hsa-miR-7-1, and hsa-miR-16-2 were previously related to adrenocortical carcinoma. According to the HMDD, none of the 8 miRNAs has been described in CIS/RRMS so far. However, hsa-miR-22, one of the 5 miRNAs in the present screening, has previously been reported as up-regulated in plasma and CD4+CD25+ regulatory T cells of patients with MS as compared to controls. Furthermore, when comparing the present results with our own initial study on multiple sclerosis, significant overlaps were detected. In detail, we identified hsa-miR-629 (p=0.0009) as well as hsa-miR-100 (p=0.04) as significantly up-regulated in MS, while we showed hsa-miR-20a to be down-regulated (p=0.0009). Likewise, hsa-miR-125b was up-regulated, although barely missing the significance threshold of 0.05 (p=0.06). The overlap between an initial study and the present work appears quite remarkable, given that different experimental set-ups were used (different microarray platforms) and completely independent cohorts (not all patients treatment-naïve, no age and sex matched controls) were studied.

In summary, a comprehensive analysis of miRNA expression in blood of treatment-naïve MS patients is shown, including CIS patients and RRMS patients, in comparison to age and sex matched control individuals. Applying NGS and microarray analyses a set of 8 miRNAs was identified, with 5 miRNAs that were up-regulated (hsa-miR-22-5p, hsa-miR-125b-5p, hsa-miR-629-5p, hsa-miR-16-2-3p, and hsa-miR-100-5p) and three miRNAs that were down-regulated (hsa-miR-20a-5p, hsa-miR-151a-3p, and hsa-miR-7-1-3p) in blood of MS patients. Using qRT-PCR we were able to confirm these results for all but one miRNA (hsa-miR-629-5p). According to the HMDD the 8 miRNAs have never been related to MS so far. However, one miRNA has previously been reported as up-regulated in plasma and regulatory T cells of MS patients. A comparison without previous data on MS we detected significant overlap. Enrichment analyses revealed that half of the miRNAs were associated with immune response, hormone regulation or adrenocortical carcinoma, respectively. The results revealed a set of miRNAs that are likely to serve as potentially useful biomarker for diagnosis, for monitoring disease activity or for the evaluation of treatment responses in patients with MS. The marker combination that has been identified allows for a simple, straightforward, reliable diagnostic test. Further molecular biological analyses on those miRNAs might help to improve the understanding of this multifactorial disease.

TABLE 1

Characteristics of patients included in this study. The last three columns indicate with an "x" the samples that were used for microarray, NGS and/or qRT-PCR. The last two lines indicate the overall distribution for patients and controls. MS patients are given separately as CIS and RRMS.

| Sample # | gender | age | sample type | micro-array | NGS | qRT-PCR |
|---|---|---|---|---|---|---|
| 1 | female | 20 | CIS_1 | x | | |
| 2 | female | 24 | RRMS_1 | x | | |
| 3 | female | 35 | | x | | |
| 4 | female | 29 | CIS_2 | x | | |
| 5 | female | 33 | RRMS_2 | x | | |
| 6 | female | 41 | | x | | |
| 7 | female | 30 | CIS_3 | x | | |
| 8 | female | 37 | | x | | |
| 9 | male | 20 | RRMS_3 | x | | |
| 10 | male | 22 | | x | | |
| 11 | male | 23 | | x | X | |
| 12 | male | 41 | CIS_4 | x | | |
| 13 | female | 24 | | x | X | |
| 14 | female | 30 | RRMS_4 | x | | |
| 15 | female | 21 | | x | X | |
| 16 | female | 46 | RRMS_5 | x | | |
| 17 | female | 24 | | x | X | |
| 18 | female | 29 | RRMS_6 | x | | |
| 19 | female | 31 | CIS_5 | x | | |
| 20 | female | 35 | RRMS_7 | x | | |
| 21 | female | 23 | CIS_6 | x | X | |
| 22 | female | 24 | | x | X | x |
| 23 | female | 42 | CIS_7 | x | X | |
| 24 | female | 24 | CIS_8 | x | | |
| 25 | female | 32 | | x | | |
| 26 | female | 21 | | x | X | |
| 27 | male | 47 | | x | X | |
| 28 | female | 25 | | x | X | x |
| 29 | female | 35 | RRMS_8 | x | | |
| 30 | female | 22 | | x | | |
| 31 | female | 41 | | x | | |
| 32 | female | 20 | CIS_9 | x | | |
| 33 | female | 41 | CIS_10 | x | X | x |
| 34 | male | 28 | CIS_11 | x | X | x |
| 35 | female | 24 | RRMS_9 | x | X | x |
| 36 | female | 30 | | x | X | x |
| 37 | male | 43 | | x | X | |
| 38 | female | 43 | RRMS_10 | x | | |
| 39 | male | 25 | CIS_12 | x | X | |
| 40 | male | 32 | | x | X | x |
| 41 | female | 45 | | x | | |
| 42 | female | 21 | | x | X | |
| 43 | female | 21 | | x | X | |
| 44 | female | 23 | | x | | |
| 45 | male | 46 | CIS_13 | x | X | x |
| 46 | female | 47 | RRMS_11 | x | | |
| 47 | male | 32 | RRMS_12 | x | X | x |
| 48 | female | 44 | RRMS_13 | x | | |
| 49 | female | 24 | | x | | |
| 50 | female | 28 | | x | X | |
| 51 | female | 47 | | x | | |
| 52 | female | 26 | | x | | |
| 53 | female | 48 | CIS_14 | x | | |
| 54 | female | 50 | CIS_15 | x | | |
| 55 | female | 23 | | x | | |
| 56 | male | 36 | RRMS_14 | x | X | x |
| 57 | female | 28 | | x | | |
| 58 | female | 28 | RRMS_15 | x | | |
| 59 | male | 23 | | x | X | |
| 60 | female | 42 | RRMS_16 | x | | |
| 61 | female | 44 | | x | X | x |
| 62 | female | 28 | CIS_16 | x | | |
| 63 | female | 31 | RRMS_17 | x | | |
| 64 | male | 54 | | x | | |
| 65 | male | 42 | RRMS_18 | x | | |
| 66 | female | 30 | CIS_17 | x | X | x |
| 67 | female | 25 | | x | | |
| 68 | female | 40 | RRMS_19 | x | | |
| 69 | female | 33 | | x | | |
| 70 | female | 51 | | | | |
| 71 | male | 30 | | x | | |
| 72 | female | 26 | | x | | |
| 73 | male | 44 | RRMS_20 | x | X | x |
| 74 | male | 53 | CIS_18 | x | | |
| 75 | female | 33 | | x | | |
| 76 | female | 34 | | x | | |
| 77 | male | 53 | RRMS_21 | x | | |
| 78 | female | 32 | RRMS_22 | x | | |
| 79 | female | 27 | CIS_19 | x | X | |
| 80 | female | 32 | | x | | |
| 81 | female | 31 | RRMS_23 | | | |
| 82 | female | 30 | CIS_20 | x | X | x |
| 83 | male | 39 | | | | |
| 84 | female | 39 | | | | |
| 85 | female | 46 | | x | X | |
| 86 | female | 32 | CIS_21 | x | | |
| 87 | male | 42 | | x | X | x |
| 88 | female | 31 | | x | X | x |
| 89 | male | 43 | | x | X | x |
| 90 | female | 28 | RRMS_24 | x | X | x |
| 91 | female | 28 | CIS_22 | x | X | |
| 92 | female | 54 | | x | | |
| 93 | male | 27 | | x | X | x |
| 94 | male | 56 | | x | X | |
| 95 | male | 29 | CIS_23 | x | | |
| 96 | male | 47 | CIS_24 | x | X | |
| 97 | female | 34 | CIS_25 | x | | |
| 98 | female | 42 | | x | | |
| 99 | male | 42 | | x | | |
| 100 | male | 24 | RRMS_25 | x | | |
| patients | 36 female/14 male | 31.5 (20-53) | 50 | 49 | 15 | 10 |
| controls | 36 female/14 male | 32 (21-56) | 50 | 47 | 23 | 10 |

TABLE 2a miRNAs deregulated in NGS and microarray analysis and validated using qRT-PCR. For the NGS analyses the read counts are given, for the microarray analyses the signal intensity values are given, and for the qRT-PCR the Ct values are given. Red fond indicates up-regulation of the respective miRNA in MS, green fond indicates down-regulation in MS compared to controls. Please note for the Ct values, that higher values mean lower expression.

| miRNA | NGS | | | microarray | | | qRT-PCR | | |
|---|---|---|---|---|---|---|---|---|---|
| | control | MS | p-value | control | MS | p-value | control | MS | p-value |
| hsa-miR-22-5p | 6 | 9.681 | 0.004 | 1034.25 | 1075.84 | 0.594 | 7.51 | 6.93 | 0.641 |
| hsa-miR-125b-5p | 4.806 | 14.444 | 0.018 | 22.979 | 42.036 | 0.156 | 5.32 | 3.71 | 0.008 |
| hsa-miR-629-5p | 4.847 | 8.958 | 0.024 | 8.385 | 9.988 | 0.224 | 7.53 | 7.7 | 0.71 |
| hsa-miR-16-2-3p | 418.792 | 793.625 | 0.05 | 26.77 | 50.538 | 0.001 | 7.45 | 6.39 | 0.036 |
| hsa-miR-100-5p | 3.993 | 44.25 | 0.04 | 12.678 | 26.817 | 0.355 | 7.37 | 4.27 | 0.019 |
| hsa-miR-20a-5p | 7.194 | 6.847 | 0.049 | 255.718 | 96.802 | 0.018 | 2.07 | 3.13 | 0.349 |
| hsa-miR-151a-3p | 580.403 | 455.056 | 0.009 | 51.266 | 43.992 | 0.61 | 2.04 | 2.56 | 0.364 |
| hsa-miR-7-1-3p | 2.681 | 0.563 | 0.001 | 3.106 | 0.1 | 0.02 | 5.57 | 6.38 | 0.169 |

TABLE 2b miRNA sequences

| SEQ ID NO | miRNA | Sequence |
|---|---|---|
| 1 | hsa-miR-22-5p | aguucuucaguggcaagcuuua |
| 2 | hsa-miR-125b-5p | ucccugagacccuaacuuguga |
| 3 | hsa-miR-629-5p | uggguuuacguugggagaacu |
| 4 | hsa-miR-16-2-3p | ccaauauuacugugcugcuuua |
| 5 | hsa-miR-100-5p | aacccguagauccgaacuugug |
| 6 | hsa-miR-20a-5p | uaaagugcuuauagugcagguag |
| 7 | hsa-miR-151a-3p | cuagacugaagcuccuugagg |
| 8 | hsa-miR-7-1-3p | caacaaaucacagucugccaua |

The invention claimed is:

1. A method for treating relapsing and remitting multiple sclerosis (RRMS) in a patient in need thereof at the clinical isolated syndrome (CIS) stage of RRMS, said method comprising:
administering an immunomodulatory or immunosuppressive therapy to the CIS stage patient, wherein a sample taken from the patient before administration of the therapy is measured by next generation sequencing and exhibits:
more than 6 read counts for hsa-miR-22-5p;
more than 4.806 read counts for hsa-miR-125b-5p;
more than 4.847 read counts for hsa-miR-629-5p;
more than 418.792 read counts for hsa-miR-16-2-3p;
more than 3.993 read counts for hsa-miR-100-5p;
fewer than 7.194 read counts for hsa-miR-20a-5p;
fewer than 580.403 read counts for hsa-miR-151a-3p; or
fewer than 2.681 read counts for hsa-miR-7-1-3p.

2. The method according to claim 1, wherein the sample is selected from the group consisting of a blood sample, a serum sample, and a plasma sample.

3. The method according to claim 1, wherein hsa-miR-16-2-3p, hsa-miR-20a-5p, and hsa-miR-7-1-3p are measured.

4. The method according to claim 1, wherein hsa-miR-16-2-3p, hsa-miR-22-5p, hsa-miR-125b-5p, hsa-miR-100-5p, hsa-miR-20a-5p, hsa-miR-151a-3p, and hsa-miR-7-1-3p are measured.

5. The method according to claim 1, wherein miR-16-2-3p, hsa-miR-22-5p, hsa-miR-125b-5p, hsa-miR-629-5p, hsa-hsa-miR-100-5p, hsa-miR-20a-5p, hsa-miR-151a-3p, and hsa-miR-7-1-3p are measured.

6. The method according to claim 1, further comprising measuring expression of hsa-miR-22-5p, hsa-miR-125b-5p, hsa-miR-629-5p, hsa-miR-16-2-3p, hsa-miR-100-5p, hsa-miR-20a-5p, hsa-miR-151a-3p, and hsa-miR-7-1-3p in the patient sample by next generation sequencing.

* * * * *